United States Patent [19]

Van Hijfte et al.

[11] Patent Number: 4,500,336

[45] Date of Patent: Feb. 19, 1985

[54] PROCESS FOR MAKING GRANULES CONTAINING UREA AS THE MAIN COMPONENT

[75] Inventors: Willy H. P. Van Hijfte, Assenede; Luc A. Vanmarcke, Kaprijke-Lembeke, both of Belgium

[73] Assignee: Compagnie Neerlandaise de l'Azote (Societe Anonyme), Belgium

[21] Appl. No.: 390,044

[22] Filed: Jun. 18, 1982

[30] Foreign Application Priority Data

Jul. 3, 1981 [NL] Netherlands .................. 8103210
Feb. 12, 1982 [NL] Netherlands .................. 8200552

[51] Int. Cl.³ ............................ C05G 3/00; C05C 9/00
[52] U.S. Cl. ............................................ 71/29; 71/30; 427/182; 427/213
[58] Field of Search .......................... 71/28-30, 71/64.06; 427/182, 213, 421; 564/63

[56] References Cited

U.S. PATENT DOCUMENTS 4,219,589 8/1980 Niks et al. ................. 71/28 X

OTHER PUBLICATIONS

Derwent Abstract 17560, Wolf, 12-10-80.

*Primary Examiner*—Ferris H. Lander
*Attorney, Agent, or Firm*—Scully, Scott, Murphy & Presser

[57] ABSTRACT

A process for making granules containing urea as the main component by prilling or granulating a urea melt or an aqueous urea solution, which melt or solution may contain one or more other fertilizers, such as ammonium sulphate, ammonium dihydrogen phosphate and diammonium hydrogen phosphate, in solution and/or suspension. According to the invention, a water-soluble aluminum salt is added to the melt, solution or suspension to be prilled or granulated. Preferably the aluminum salt is added in a quantity equivalent to at least 0.1% by weight of $Al_2O_3$, calculated on the solid content of the melt, solution or suspension.

2 Claims, No Drawings

PROCESS FOR MAKING GRANULES CONTAINING UREA AS THE MAIN COMPONENT

Various methods are known for making urea granules. One of these is prilling, which is here understood to mean a method in which a substantially anhydrous urea melt (with a water content of no more than 0.1 to 0.3% by weight) is sprayed in the top of a prilling tower in a rising stream of air of ambient temperature, in which the droplets solidify. The resulting prills have a maximum diameter of approximately 2 mm and are mechanically rather weak.

Urea granules having larger dimensions and better mechanical properties can be produced by the granulation of a substantially anhydrous urea melt in a drum granulator, e.g. by the spherodizer technique, as described in British Pat. No. 894,773, or in a pan granulator, e.g. as described in U.S. Pat. No. 4,008,064, or by the granulation of an aqueous urea solution in a fluidized bed, e.g. as described in Dutch patent application No. 78,06213. In the process according to the publication last mentioned, an aqueous urea solution with a urea concentration of 70-99.9% by weight, preferably 85-96% by weight, is sprayed, in the form of very fine droplets having an average diameter of 20-120 micron, into a fluidized bed of urea particles, at a temperature at which the water from the solution sprayed onto the particles is evaporated, and urea solidifies on the particles to form granules having a desired size, which may be 25 mm and more. As rather a great deal of dust is formed in this process, epecially if the urea solution used as the starting material contains more than 5% by weight of water, in particular more than 10% by weight of water, preferably a crystallization retarder for the urea, in particular a water-soluble addition or condensation product of formaldehyde and urea, is added to the urea solution, whereby the formation of dust is practically fully suppressed. The presence of the crystallization retarder has for its result that the granules remain plastic as they are being built, so that owing to rolling and/or impacts during granule formation, mechanically strong, smooth and round granules may be formed. The granules thus produced have a high crushing strength, a high impact resistance, and a low tendency of forming dust from rubbing together, and in addition do not cake, even when stored for long periods of time, although urea has a high natural caking tendency.

Fertilizer granules are known which in addition to urea contain one or more other fertilizers. Such granules can be produced by prilling or by granulation in a drum granulator or in a pan granulator from a substantially anhydrous urea melt, containing one or more other fertilizers in finely-divided solid condition, or by the granulation in a fluidized bed of an aqueous urea solution containing one or more other fertilizers in solution and/or suspension.

Examples of fertilizers which are often processed to granules together with urea are ammonium sulphate, ammonium dihydrogen phosphate and diammonium hydrogen phosphate. Urea and ammonium sulphate containing granules serve for fertilizing lands poor in sulphur, and often contain up to 40% by weight and preferably 15-20% by weight of ammonium sulphate. Granules containing urea and ammonium dihydrogen phosphate or diammonium hydrogen phosphate are often made to consumer's specification, who requires a certain percentage of phosphate in the granules. Other fertilizers are also sometimes processed with urea into granules.

It has now been found that water-soluble aluminum compounds are good urea crystallization retarders, and that granules produced by prilling or granulating a urea melt or solution containing such a crystallization retarder have particular properties, even if the urea melt or solution contains one or more other fertilizers in solution and/or suspension.

The invention accordingly relates to a process for making granules containing urea as the main component by prilling or granulating a urea melt or an aqueous urea solution, which melt or solution may contain one or more other fertilizers, such as ammonium sulphate, ammonium dihydrogen phosphate, and diammonium hydrogen phosphate, in solution and/or suspension, said process being characterized in that a water-soluble aluminum salt is added to the melt, solution, or suspension to be prilled or granulated.

It has surprisingly been found, that the presence of a water-soluble inorganic aluminum salt during the prilling or granulation has for its result that the building-up of the granules proceeds well, and the formation of flydust is prevented, while in addition the resulting granules have a high crushing strength, a high apparent specific gravity, and a greatly reduced caking tendency, and in some cases do not even cake together when stored for prolonged periods of time. Furthermore it is found that the granules produced according to the invention are compatible with single and triple superphosphate granules (SSP and TSP, respectively), which make them suitable for bulk blending with these phosphate fertilizers.

Conventional urea granules are known to be unsuitable for use in heterogeneous binary and ternary fertilizer mixtures, such as N-P or N-P-K mixtures, by bulk blending with a cheap single or triple superphosphate, as such urea granules are incompatible with these phosphates. Mixtures of such urea granules with single or triple superphosphate granules deliquesce after some time forming an unmanageable and unusable mud. According to a paper presented by G. Hoffmeister and G. H. Megar during "The Fertilizer Industry Round Table" at Washington, D. C. on Nov. 6, 1975, this incompatibility is caused by a reaction according to the following equation:

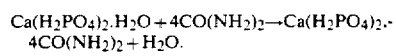

$$Ca(H_2PO_4)_2.H_2O + 4CO(NH_2)_2 \rightarrow Ca(H_2PO_4)_2.4CO(NH_2)_2 + H_2O.$$

Owing to the reaction of 1 mole monocalcium phosphate monohydrate, the main component of SSP and TSP, with 4 moles of urea, a urea monocalcium phosphate adduct is formed, whereby 1 mole of water is liberated. As the adduct is very soluble, it is readily dissolved in the water released to form a large volume of solution, which moistens the granules in the mixture, owing to which the reaction proceeds ever faster. No commercially acceptable means are known for rendering urea compatible with SSP and TSP. Indeed, for bulk blending with urea the more expensive phosphate fertilizers monoammonium phosphate and diammonium phosphate have hitherto been used.

The granules produced according to the invention, however, which contain urea as their main component, are compatible with SSP and TSP granules in all ratios, which make them suitable for bulk blending with these phosphate fertilizers.

Examples of water-soluble inorganic aluminum salts that can be used in the process according to the invention are aluminum chloride, aluminum sulphate and alkaline aluminum sulphate, $NaAl(SO_4)_2$. The aluminum salt is added to the urea melt or solution to be prilled or granulated in a proportion equivalent to at least 0.1% by weight $Al_2O_3$, preferably equivalent to 0.4–1% by weight $Al_2O_3$, calculated on the solid content of the melt or solution. Proportions of more than 1.5% by weight, calculated as $Al_2O_3$, are not harmful, but do not offer any particular advantages. The additive may be added in the form of a powder or, if an aqueous solution or supension is granulated, if desired in the form of an aqueous solution or suspension.

Preferably, after their formation, the granules are cooled to 30° C. or to a lower temperature, for example, by means of an air stream whose moisture content has preferably being reduced so that during cooling the granules do not absorb any moisture from the cool air.

The invention also relates to compatible, heterogeneous fertilizer mixtures of urea-containing granules produced by the process according to the invention with SSP and TSP granules and, if desired, one or more other granular substances.

In addition to granules containing urea and SSP or TSP granules, generally a potassium fertilizer is included in the mixture, such as KCl. In order to prevent segregation of the mixture, the particle sizes of the components to be blended should be adapted to each other.

For further information regarding the manufacture of fertilizer granules, reference is made, for the prilling process, to U.S. Pat. No. 3,130,225, for granulation in a pan granulator to U.S. Pat. No. 4,008,064, for the granulation in a drum granulator to British Pat. No. 894,773, and for the granulation in a fluidized bed to Dutch patent application No. 78,06213.

If the granulation is carried out in a fluidized bed, the starting material used is an aqueous urea solution with a urea concentration of at least 70% by weight and preferably 85–96% by weight. For the granulation of urea together with one or more other fertilizers, preferably a urea solution with a urea concentration of 90–95% by weight is used, to which the other fertilizer is added in the solid state, preferably in finely-divided form, or as an aqueous solution. The solubility of the fertilizers to be added in the aqueous urea solution varies. Thus the solubility of ammonium sulphate in a 95% by weight urea solution is 12%, and in a 90% by weight urea solution 20%. Ammonium dihydrogen phosphate and diammonium hydrogen phosphate can form highly viscous solutions with 90–95% by weight urea solutions, which are difficult to be sprayed. This can be prevented by passing the urea solution and an aqueous solution of the phosphate separately to the sprayers and mixing them together for a short period of time only before the mixture is sprayed.

EXAMPLE I

The effect of the process according to the invention is demonstrated by the following tests, in which an aqueous urea solution without and with a known crystallization retarder and with a water-soluble inorganic aluminum salt as a crystallization retarder was sprayed into a fluidized bed of urea particles. The granulation conditions and the physical properties of the resulting granules are listed in the following table.

The "TVA Bottle Test" referred to in Table A serves for determining the compatibility of urea granules with SSP and TSP granules. In this test, the condition of a mixture of the urea granules to be tested with SSP or TSP granules, kept in a closed bottle of 120 $cm^3$ at 27° C. was periodically inspected. So long as the mixture did not exhibit more than some moisture spots, it was qualified as suitable for use.

By means of the "bag test" referred to in Table A the caking tendency of the granules tested was determined. In this test, urea granules were packed in bags of 35 kg, which were stored at 27° C. under a weight of 1000 kg. After 1 month, the percentage by weight of the lumps per bag was determined, and the average hardness of the lumps was measured. Hardness as used in this context means the force in kg, exerted by a dynamometer for disintegrating a lump of $7 \times 7 \times 5$ cm.

The crystallization retarder F 80, mentioned in Table A is a clear viscous liquid commercially available under the name of "Formurea 80", which is stable between $-20°$ C. and $+40°$ C. and, upon analysis, is found to contain per 100 parts by weight approximately 20 parts of water, approximately 23 parts of urea and approximately 57 parts of formaldehyde, approximately 55% of the amount of formaldehyde being bound as trimethylolurea, and the balance being present in the non-combined condition.

TABLE A

| Test No. | 1 | 2 | 3 | 4 | 5 |
|---|---|---|---|---|---|
| Crystallisation retarder | none | F 80 1% | $AlCl_3.6H_2O$ 2% | $Al_2(SO_4)_3.17H_2O$ 2.5% | alkaline Al sulphate 2% |
| Granulation conditions | | | | | |
| urea solution | | | | | |
| concentration, wt % | 94.6 | 94.5 | 95.5 | 95.5 | 95.5 |
| temperature, °C. | 130 | 130 | 130 | 130 | 130 |
| rate, kg/uur | 280 | 280 | 280 | 220 | 220 |
| spraying air | | | | | |
| rate, $Nm^3$/hour | 130 | 130 | 130 | 130 | 130 |
| temperature, °C. | 140 | 140 | 148 | 149 | 148 |
| fluidisation air | | | | | |
| rate, $Nm^3$/hour | 850 | 850 | 850 | 850 | 850 |
| temperature, °C. | 45 | 64 | 60 | 65 | 63 |
| bed temperature, °C. | 108 | 105 | 107 | 99 | 105 |
| Product properties | | | | | |
| apparent density, g/$cm^3$ | 1.23 | 1.26 | 1.29 | 1.30 | 1.28 |
| crushing strength dia. 2.5 mm, kg | 2.1 | 2.8 | 3.1 | 3.0 | 2.9 |

TABLE A-continued

| Test No. | 1 | 2 | 3 | 4 | 5 |
|---|---|---|---|---|---|
| Crystallisation retarder | none | F 80 1% | AlCl$_3$.6H$_2$O 2% | Al$_2$(SO$_4$)$_3$.17H$_2$O 2.5% | alkaline Al sulphate 2% |
| dust, g/kg bag test | 5.4 | <0.1 | <0.1 | <0.1 | <0.1 |
| lumps, % | 100 | 10 | 45 | 0 | 0 |
| hardness, kg | 22 | <1 | 3.3 | 0 | 0 |
| TVA Bottle Test |  |  |  |  |  |
| with SSP 50/50 suitability, days | <3 | <3 | >60 | >60 | >60 |
| with TSP 50/50 suitability, days | <3 | <3 | >60 | >60 | >60 |

EXAMPLE II

In a further series of tests, a substantially anhydrous urea melt with and without added aluminum sulphate was sprayed in the top of a prilling tower in a rising stream of air of ambient temperature.

The physical properties of the resulting prills are listed in Table B.

TABLE B

| Additive | none | aluminum sulphate | | |
|---|---|---|---|---|
|  | none | 0.63% | 1.1% | 1.5% |
| Product properties |  |  |  |  |
| apparent density, g/cm$^3$ | 1.30 | 1.31 | 1.30 | 1.30 |
| crushing strength dia. 2.5 mm, kg | 0.54 | 0.70 | 0.98 | 1.08 |
| bag test |  |  |  |  |
| lumps, % | 100 | 10 | 25 | 0 |
| hardness, kg | 9 | 1.5 | 2.5 | 0 |
| TVA Bottle Test |  |  |  |  |
| with SSP 50/50 suitability for use, days | <3 | 14 | >60 | >60 |
| with TSP 50/50 suitability for use, days | <3 | 14 | >60 | >60 |

EXAMPLE III

An aqueous urea melt (99.8 wt. % urea), to which 2 wt% Al$_2$(SO$_4$)$_3$.17H$_2$O had been added, was granulated in a rotary, horizontal granulation drum with a diameter of 90 cm and a width of 60 cm. The drum was provided on its inner wall with eight uniformly spaced longitudinal strips of 3.5 × 60 cm. The drum was rotated at a rate of 15 rpm. The drum was filled with 60 kg urea granules having an average diameter of 1.9 mm and a temperature of 80° C. By means of two hydraulic sprayers 60 kg of the urea melt with a temperature of 140°-145° C. was sprayed into the rotating drum at a rate of approximately 120 kg/hour over the granules, which showered off the longitudinal strips. The granulation took place at 108° C. At the end of the test, the granules were cooled to approximately 30° C. and sieved. The product granules had a good roundness and a smooth surface. The apparent density was 1.279 g/cm$^3$ and the crushing strength dia. 2.5 mm was 3.3 kg. Dust formation was 0.5 g/kg. The granules exhibited virtually no caking tendency. Mixtures with SSP (50/50) and with TSP (50/50) were suitable for use for more than 60 days. The sieve analysis of the product was as follows:

| >4.00 mm | 18% |
|---|---|
| 4.00-2.5 mm | 47% |
| 2.5-2.0 mm | 31% |
| <2.0 mm | 4% |
| average diameter | 3.4 mm |

EXAMPLE IV

In a number of granulation tests, a suspension of finely-ground ammonium sulphate in a 95 wt% aqueous urea solution with a known crystallization retarder (F 80) and with aluminum sulphate as a crystallization retarder was sprayed into a fluidized bed of urea particles. The ammonium sulphate content of the suspension was 20% by weight.

The suspension was sprayed at a temperature of 120°-130° C. and at a rate of approximately 300 kg/hour. Spraying was effected by means of spraying air having a temperature of 140° C. under an overpressure of 0.35 kg/cm$^2$ and at a rate of approximately 140 Nm$^3$/hour. The bed was fluidized with air at a rate of 650-850 Nm$^3$/hour. The temperature of the fluidization air was controlled so that the temperature of the bed was maintained between 105° and 108° C.

In all tests, granule build-up in the fluidized bed proceeded excellently. The product contained only very little fine material, which means that the sprayed suspension was used practically entirely for the build-up of the granules. The chemical and physical properties of the resulting granules are listed in the following table.

TABLE C

| Crystallization retarder | 1% F 80 | | | 1% aluminum sulphate[x] | | |
|---|---|---|---|---|---|---|
| Chemical properties: |  |  |  |  |  |  |
| moisture, wt % | 0.18 | 0.13 | 0.21 | 0.12 | 0.12 | 0.12 |
| ammonium sulphate, wt % | 13.7 | 15.0 | 18.5 | 16.0 | 19.5 | 18.8 |
| pH of 10 wt % solution | 5.2 | 5.0 | 5.1 | 5.2 | 5.0 | 5.0 |
| Physical properties: |  |  |  |  |  |  |
| crushing strength dia. 2.5 mm, kg | 3.3 | 3.4 | 3.5 | 3.8 | 3.9 | 4.0 |
| bag test |  |  |  |  |  |  |
| lumps, % | 48 | 25 | 35 | 0 | 0 | 0 |
| hardness, kg | 2.2 | 2.5 | 4.0 | 0 | 0 | 0 |
| TVA Bottle Test |  |  |  |  |  |  |
| with SSP 50/50 suitability for use, days | <3 | <3 | <3 | >60 | >60 | >60 |
| with TSP 50/50 suitability for use, days | <3 | <3 | <3 | >60 | >60 | >60 |

[x]calculated as the anhydrous salt

We claim:

1. In a process for preparing granules containing urea as the main component by spraying an aqueous urea solution having a urea concentration of 85–98% by weight, to which said solution is added a crystallization retarder for the urea, said solution optionally containing other fertilizers including ammonium sulphate, ammonium dihydrogen phosphate, and diammonium hydrogen phosphate in solution or suspension, in the form of fine droplets having an average diameter between 20 and 120 microns, into a fluidized bed of urea particles at a temperature at which the water from the solution or suspension sprayed onto the particles is evaporated and the urea or fertilizer material containing urea as the main component solidifies on the particles to form granules having the desired size, the improvement comprising using a crystallization retarder consisting essentially of a water-soluble aluminum salt, wherein said aluminum salt is added to the solution or suspension in an amount equivalent to at least 0.1 to about 1.0% by weight of $Al_2O_3$ calculated on the urea in said solution or suspension.

2. Compatible heterogeneous fertilizer mixtures of urea containing granules prepared by the process of claim 1 further comprising single or triple superphosphate granules and, optionally, other granular fertilizers including KCl.

* * * * *